United States Patent
Shibata et al.

(10) Patent No.: US 9,687,144 B2
(45) Date of Patent: Jun. 27, 2017

(54) FUNDUS PHOTOGRAPHING APPARATUS WITH WAVEFRONT COMPENSATION AND METHOD FOR PHOTOGRAPHING FUNDUS IMAGE

(71) Applicant: NIDEK CO., LTD., Aichi (JP)

(72) Inventors: Naohisa Shibata, Aichi (JP); Yuji Yamazaki, Aichi (JP); Masaaki Hanebuchi, Aichi (JP); Yuki Yoshihara, Aichi (JP)

(73) Assignee: NIDEK CO., LTD., Aichi (JP)

( * ) Notice: Subject to any disclaimer, the term of this patent is extended or adjusted under 35 U.S.C. 154(b) by 0 days.

(21) Appl. No.: 14/869,173

(22) Filed: Sep. 29, 2015

(65) Prior Publication Data

US 2016/0089016 A1 Mar. 31, 2016

(30) Foreign Application Priority Data

Sep. 30, 2014 (JP) ................ 2014-202560

(51) Int. Cl.
*A61B 3/14* (2006.01)
*A61B 3/00* (2006.01)
*A61B 3/12* (2006.01)
*A61B 3/10* (2006.01)

(52) U.S. Cl.
CPC .......... *A61B 3/0025* (2013.01); *A61B 3/1015* (2013.01); *A61B 3/12* (2013.01); *A61B 3/14* (2013.01)

(58) Field of Classification Search
USPC ................................ 351/200–246
See application file for complete search history.

(56) References Cited

U.S. PATENT DOCUMENTS

| | | | |
|---|---|---|---|
| 5,572,266 A | * | 11/1996 | Ohtsuka ............... A61B 3/145 351/208 |
| 5,777,719 A | | 7/1998 | Liang |
| 5,949,521 A | | 9/1999 | Liang |
| 6,095,651 A | | 8/2000 | Liang |
| 6,379,005 B1 | | 4/2002 | Liang |
| 2003/0025874 A1 | | 2/2003 | Liang |
| 2006/0044510 A1 | | 3/2006 | Liang |
| 2008/0151189 A1 | * | 6/2008 | Iwa ......................... A61B 3/12 351/206 |
| 2008/0251955 A1 | | 10/2008 | Liang |
| 2008/0259273 A1 | | 10/2008 | Liang |

(Continued)

FOREIGN PATENT DOCUMENTS

JP 2001507258 6/2001
JP 2011115301 A2 6/2011

(Continued)

*Primary Examiner* — Mohammed Hasan
(74) *Attorney, Agent, or Firm* — Rankin, Hill & Clark LLP

(57) ABSTRACT

A method for photographing a fundus image includes: acquiring photographing condition data on a first captured image being a cell image of a fundus as reference data for follow-up image capture related to the cell image, and storing the photographing condition data; and selecting, based on an operation input from an examiner, reference data for the follow-up image capture from one or more pieces of the reference data stored in advance, and reproducing a photographing condition in accordance with the selected reference data to newly acquire the cell image.

9 Claims, 12 Drawing Sheets

(56) References Cited

U.S. PATENT DOCUMENTS

2008/0316429 A1    12/2008   Liang
2009/0002628 A1     1/2009   Liang
2010/0296056 A1*   11/2010   Uchida .................... A61B 3/14
                                                                               351/206

FOREIGN PATENT DOCUMENTS

JP         2014110825 A2    6/2014
WO        9827863 A1    7/1998

\* cited by examiner

FUNDUS PHOTOGRAPHING APPARATUS WITH WAVEFRONT COMPENSATION AND METHOD FOR PHOTOGRAPHING FUNDUS IMAGE

CROSS-REFERENCE TO RELATED APPLICATION

This application claims priority from Japanese Patent Application No. 2014-202560 filed with the Japan Patent Office on Sep. 30, 2014, the entire content of which is hereby incorporated by reference.

BACKGROUND

1. Technical Field

The present disclosure relates to a fundus photographing apparatus with wavefront compensation that photographs a fundus image of an examinee's eye, and a method for photographing the fundus image.

2. Related Art

In a known fundus photographing apparatus, for example, a wavefront sensor such as a Shack-Hartmann sensor is used to detect the wavefront aberrations of an eye. Furthermore, a wavefront compensating device is controlled based on the detection result, and a fundus image after wavefront compensation is captured at a cell level. The fundus image obtained by such a device can be used for, for example, image processing related to fundus cells, such as cell density analysis (see, for example, JP-A-2014-110825).

SUMMARY

A fundus photographing apparatus with wavefront compensation includes: a fundus imaging optical system that receives a reflected light from fundus of an examinee's eye with a light receiving device to acquire a cell image of the fundus; a wavefront compensating device placed in an optical path of the fundus imaging optical system to compensate for wavefront aberrations of the examinee's eye by controlling a wavefront of the reflected light; and a controller that executes a photographing step that acquires a first captured image being a captured image of the cell image based on a signal from the light receiving device in a state where the wavefront aberrations are compensated for, a reference data registration step that acquires photographing condition data on the first captured image as reference data for follow-up image capture and storing the photographing condition data in a storage unit, and a photographing condition reproduction step that selects, based on an operation input from an examiner, reference data for the follow-up image capture from one or more pieces of the reference data stored in advance in the storage unit in the reference data registration step, and reproducing a photographing condition in accordance with the selected reference data to newly acquire the cell image.

A method for photographing a fundus image includes: acquiring photographing condition data on a first captured image being a cell image of a fundus as reference data for follow-up image capture related to the cell image, and storing the photographing condition data; and selecting, based on an operation input from an examiner, reference data for the follow-up image capture from one or more pieces of the reference data stored in advance, and reproducing a photographing condition in accordance with the selected reference data to newly acquire the cell image.

DESCRIPTION OF THE EMBODIMENTS

Figure 1:
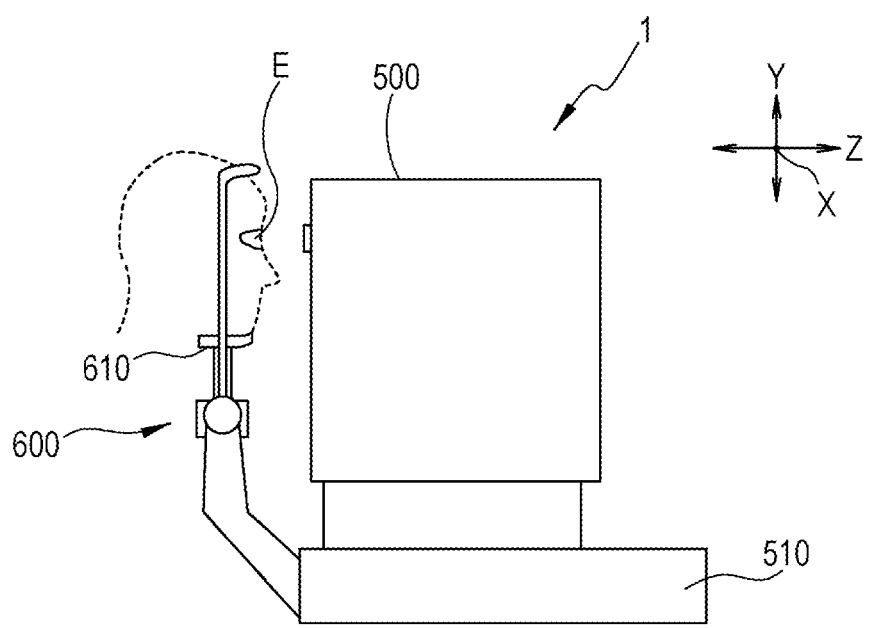
FIG. 1 is a diagram illustrating an external view of a photographing apparatus of an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

For example, in cases such as follow-up, image capturing may be desired to be performed on the same condition to compare a captured image obtained in advance and a captured image obtained later. However, in an optical system of the known photographing apparatus, an image is largely affected by a change in a positional relationship between the optical system and the eye upon each image capturing due to eye movement. Hence, it is difficult to manually reproduce the same condition as a photographing condition for the captured image obtained in advance, and captures an image for the follow-up.

An object of the present disclosure is to provide a fundus photographing apparatus with wavefront compensation and a method for photographing a fundus image that facilitates image capturing on the same photographing condition as a photographing condition for a captured image obtained in advance.

A typical embodiment will be described below with reference to the drawings. A photographing apparatus 1 is a fundus photographing apparatus with wavefront aberration compensation, which photographs a fundus image of an examinee's eye whose wavefront aberrations have been corrected (compensated for). In the following description, the case where the photographing apparatus 1 is an AOSLO (adaptive optics scanning laser ophthalmoscope) will be described as an example. The photographing apparatus 1, however, is not limited to the AOSLO (the details of which will be described later).

Firstly, a schematic configuration of the photographing apparatus 1 will be described with reference to FIG. 1. The photographing apparatus 1 includes a base 510, a face support unit 600, and a photographing unit 500. The face support unit 600 is attached to the base 510. Optical systems described below are housed in the photographing unit 500. The photographing unit 500 is provided on the base 510. A chin support 610 is provided to the face support unit 600. The chin support 610 is moved by the operation of an unillustrated chin support driving part in the right-left direction (X direction), the up-down direction (Y direction), and the front-back direction (Z direction) with respect to a base portion of the face support unit 600.

Figure 2:
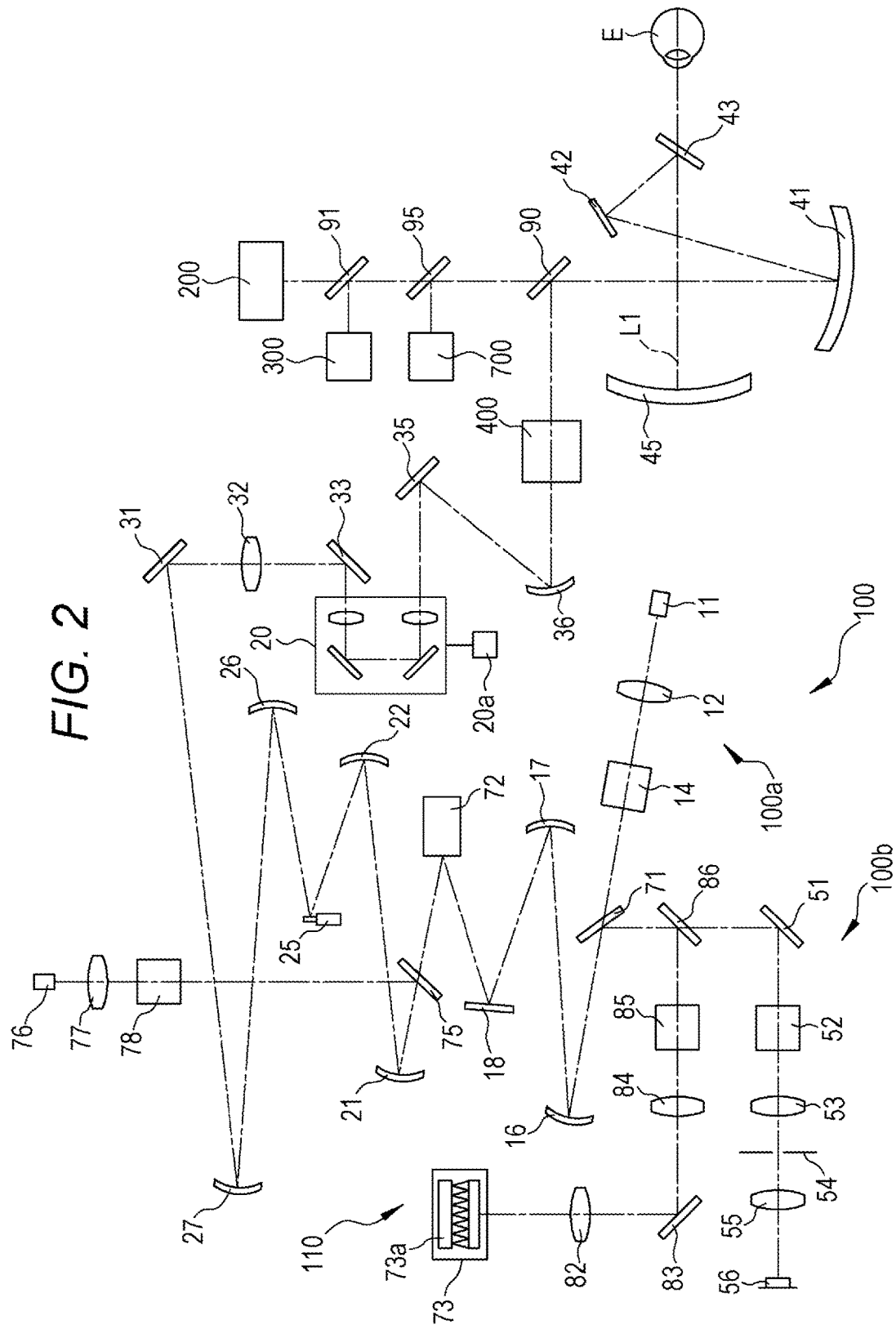
FIG. 2 is a schematic diagram illustrating optical systems of the photographing apparatus.

Next, the optical systems of the photographing apparatus 1 will be described with reference to FIG. 2. The photographing apparatus 1 of the embodiment includes a fundus imaging optical system 100, a wavefront aberration detecting optical system (hereinafter described as an aberration detecting optical system) 110, aberration compensating units 20 and 72, a second photographing unit 200, a tracking purpose unit (position detecting unit) 300, and an anterior segment observing unit 700.

The fundus imaging optical system 100 projects laser light (illuminating light) to an examinee's eye E. Furthermore, the fundus imaging optical system (first photographing unit) 100 receives reflected laser light from the fundus and captures a fundus image of the examinee's eye E. The fundus of the examinee's eye E is photographed by the fundus imaging optical system 100 at a high resolution (high resolving power) and a high magnification. As described below, the fundus imaging optical system 100 may have, for example, a configuration of a scanning laser ophthalmoscope using a confocal optical system. The fundus imaging optical system 100 includes a first illuminating optical system 100a and a first photographing optical system 100b. Moreover, in the embodiment, the aberration compensating units 20 and 72 are placed in the fundus imaging optical system 100 to correct (compensate for) the aberrations of the examinee's eye. The aberration compensating units are broadly divided into a correction optical system for correcting low-order aberrations, equal to or lower than second order, of the examinee's eye, and a high-order aberration compensating unit (wavefront compensating device) 72 for correcting high-order aberrations of the examinee's eye. In the embodiment, as an example, the diopter correction unit 20 that corrects a diopter (for example, spherical power) is used as the correction optical system that corrects low-order aberrations equal to or lower than second order.

The first illuminating optical system 100a irradiates the examinee's eye E with laser light and scans the laser light over the fundus, so as to illuminate the fundus two-dimensionally. The first illuminating optical system 100a includes, in an optical path from a light source 11 (first light source) to the fundus, the light source 11, a lens 12, a polarizing beam splitter (PBS) 14, a beam splitter (BS) 71, a concave mirror 16, a concave mirror 17, a planar mirror 18, the aberration compensating unit 72 (wavefront compensating device 72), a beam splitter (BS) 75, a concave mirror 21, a concave mirror 22, a scanning unit 25, a concave mirror 26, a concave mirror 27, a planar mirror 31, a lens 32, a planar mirror 33, the aberration compensating unit 20 (diopter correction unit 20), a planar mirror 35, a concave mirror 36, a deflecting unit 400, a dichroic mirror 90, a concave mirror 41, a planar mirror 42, a planar mirror 43, and a concave mirror 45.

The light source 11 emits laser light. In the embodiment, the laser light has a wavelength in the near-infrared region.

Accordingly, it is difficult for the examinee's eye to visually recognize the laser light. For example, in the embodiment, an SLD (Super Luminescent Diode) with a wavelength of 840 nm is used as the light source 11. The light source 11 is simply required to emit spot light having a characteristic feature of a high convergence rate, and may be, for example, a semiconductor laser.

The laser light emitted from the light source 11 is changed by the lens 12 to parallel light, and then incident on the wavefront compensating device 72 via the PBS 14, the BS 71, the concave mirrors 16 and 17, and the planar mirror 18. In the embodiment, the laser light passes through the PBS 14 to be a light flux only with the S polarization component. The wavefront compensating device 72 controls the wavefront of the incident light to correct high-order aberrations of the examinee's eye. The detailed configuration of the wavefront compensating device 72 will be described below. In the embodiment, the laser light is guided from the wavefront compensating device 72 to the BS 75 and then reflected by the concave mirrors 21 and 22 to travel to the scanning unit 25.

In the embodiment, the scanning unit 25 is used together with the deflecting unit 400 to two-dimensionally scan the laser light over the fundus. The scanning unit 25 is a resonant mirror used for main scanning with laser light. The scanning unit 25 scans the fundus with the laser light in the X direction.

The light having passed the scanning unit 25 enters the diopter correction unit 20 via the concave mirrors 26 and 27, the planar mirror 31, the lens 32, and the planar mirror 33.

The diopter correction unit 20 is a unit for correcting a diopter. The diopter correction unit 20 includes two pairs of a lens and a planar mirror in addition to a driving part 20a. The planar mirrors and lenses of the diopter correction unit 20 are moved by the driving part 20a toward a predetermined direction to adjust the optical path length. As a result, an error in the diopter of the examinee's eye E is corrected.

The illuminating light guided from the diopter correction unit 20 to the planar mirror 35 is reflected by the concave mirror 36 to travel to the deflecting unit 400.

The deflecting unit 400 scans the fundus in the vertical direction (Y direction) with the laser light emitted from the light source 11. Furthermore, the deflecting unit 400 is also used to move a fundus scan range with the laser light. For example, in the embodiment, the deflecting unit 400 may include two optical scanners (as a specific example, an X galvanometer mirror and a Y galvanometer mirror) each having a different laser light deflecting direction. The deflecting unit 400 (optical scanners) may be configured to scan the fundus with light to obtain light reflected from the fundus.

The light having passed the deflecting unit 400 is guided into the pupil of the examinee's eye E through the dichroic mirror 90, the concave mirror 41, the planar mirrors 42 and 43, and the concave mirror 45. The laser light is condensed on the fundus surface of the examinee's eye E. As described above, the fundus is two-dimensionally scanned with the laser light by the operations of the scanning unit 25 and the deflecting unit 400.

Moreover, the dichroic mirror 90 has a characteristic feature of transmitting light fluxes from the second photographing unit 200 and the tracking purpose unit 300, which are described below, while reflecting light fluxes from the light source 11 and a light source 76 described below. The positions of outgoing ends of the light sources 11 and 76 and the position of the fundus of the examinee's eye E are conjugated (or substantially conjugated) with each other. In this manner, the first illuminating optical system 100a is formed.

Next, the first photographing optical system 100b will be described. The first photographing optical system 100b receives, with a light receiving device 56, reflected light of the laser light applied to the fundus. The photographing apparatus 1 acquires a first fundus image (in the embodiment, an AO-SLO image) based on a signal from the light receiving device 56. The first photographing optical system 100b shares the optical path from the examinee's eye E to the BS 71 with the first illuminating optical system 100a. Moreover, the first photographing optical system 100b includes elements arranged in an optical path on the reflection side of the BS 71, i.e., a planer mirror 51, a PBS 52, a lens 53, a pinhole plate 54, a lens 55, and the light receiving device 56. In the embodiment, an APD (avalanche photodiode) is used as the light receiving device 56. Moreover, the pinhole plate 54 is placed at a position conjugated (or substantially conjugated) with the fundus.

The fundus reflected light of the laser light from the light source 11 traces the optical path back in the above-mentioned first illuminating optical system 100a. The fundus reflected light is reflected by both the BS 71 and the planar mirror 51. Only the S-polarized light passes through the PBS 52. The transmitted light comes into focus at a pinhole of the pinhole plate 54 via the lens 53. The reflected light having come into focus at the pinhole is received by the light receiving device 56 via the lens 55. Part of the illuminating light (the laser light from the light source 11) is reflected on the cornea. However, most of the cornea reflected light is removed by the pinhole plate 54. Hence, the light receiving device 56 can suppress the influence of the cornea reflection and receive the reflected light from the fundus.

An image processor (for example, a controller 800) processes a light receiving signal of the light receiving device 56 to acquire the first fundus image. In the embodiment, a fundus image of one frame is formed by main scanning with the scanning unit 25 and by sub scanning with a galvanometer mirror for Y scanning provided to the deflecting unit 400. Deflection angles (swing angles) of mirrors of the scanning unit 25 and the deflecting unit 400 are determined in such a manner that the angle of view of the fundus image acquired by the first photographing unit 100 is a predetermined angle. Here, the angle of view is set to approximately one to five degrees to observe and photograph a predetermined area of the fundus at a high magnification (here, for example, to observe the predetermined area of the fundus at a cell level). In the embodiment, as an example, the angle of view is set to 1.5 degrees. The photographing range of the first fundus image depends on the diopter of the examinee's eye and the like, but is set to an angle of approximately 500 μm, for example.

Furthermore, the reflection angles of a galvanometer mirror for X scanning and the galvanometer for Y scanning, which are provided to the deflecting unit 400, are moved larger than the imaging view angle of the first fundus image to change the imaging position of the first fundus image on the fundus (i.e., the scan range of the laser light).

The second photographing unit 200 is a unit for acquiring a fundus image with a wider angle of view than the angle of view of the first photographing unit 100 (a second fundus image). The second fundus image is used as, for example, an image for specifying a position and confirming the position to obtain the first fundus image. The second photographing unit 200 of the embodiment is preferred to have a configuration where a fundus image of the examinee's eye E can be acquired and observed at a wide angle of view (for example, approximately 20 to 60 degrees) in real time. For example, observing and photographing optical systems of a known fundus camera and an optical system and a control system of a scanning laser ophthalmoscope (SLO) may be used as the second photographing unit 200.

The tracking purpose unit 300 detects time-varying changes of displacement due to any of fine involuntary movement during fixation, poor fixation and the like of the examinee's eye E to obtain moving position information. The tracking purpose unit 300 sends, to the controller 800, a light receiving result obtained at the start of tracking as reference information. Then, the tracking purpose unit 300 sequentially transmits, to the controller 800, a light receiving result (light receiving information) obtained upon each scan. The controller 800 compares the reference information with light receiving information subsequently obtained, and obtains moving position information by calculation so as to obtain the same light receiving information as the reference information. The controller 800 drives the deflecting unit 400 based on the obtained moving position information. With such tracking, the deflecting unit 400 is driven in such a manner that even if the examinee's eye E moves involuntarily, the movement is compensated for. Hence, the movement of the fundus image displayed on a monitor 850 is suppressed. Moreover, a dichroic mirror 91 has a characteristic feature of transmitting light fluxes from the second photographing unit 200 while reflecting light fluxes from the tracking purpose unit 300.

The anterior segment observing unit 700 is a unit that illuminates the anterior segment of the examinee's eye E and captures an anterior segment front image. The image captured by the anterior segment observing unit 700 is output to the monitor 850. The anterior segment image acquired by the anterior segment observing unit 700 is used to align the photographing unit 500 with the examinee's eye E. A dichroic mirror 95 has a characteristic feature of transmitting light fluxes from the second photographing unit 200 and the tracking purpose unit 300 while reflecting light fluxes from the anterior segment observing unit 700.

Next, the aberration detecting optical system 110 will be described. The aberration detecting optical system 110 includes a wavefront sensor 73. Moreover, the aberration detecting optical system 110 projects measurement light to the fundus of the examinee's eye E, and receives (detects) fundus reflected light of the measurement light as a target pattern image with the wavefront sensor 73. The aberration detecting optical system 110 has part of its optical devices in the optical path of the first illuminating optical system 100a and the first photographing optical system 100b (in the embodiment, the common optical path) to share part of the optical path with the optical systems 100a and 100b. In other words, the aberration detecting optical system 110 of the embodiment shares the BS 71 to the concave mirror 45, which are placed in the optical path of the optical systems 100a and 100b, with the optical systems 100a and 100b. Furthermore, the aberration detecting optical system 110 includes the light source 76, a lens 77, a PBS 78, the BS 75, the BS 71, a dichroic mirror 86, a PBS 85, a lens 84, a planar mirror 83, and a lens 82.

The light source 76 is used to detect the aberrations of the examinee's eye E. In the embodiment, the light source 76 emits light with a wavelength different from the wavelength of the light from the light source 11. As an example, in the embodiment, a laser diode that emits laser light with a wavelength of 780 nm as the measurement light is used as the light source 76. The measurement light emitted from the light source 76 is changed by the lens 77 to a parallel light flux to enter the PBS 78.

The PBS 78 is an example of a first polarizing member provided to the aberration compensating unit. The PBS 78 polarizes the light emitted from the light source 76 to a predetermined direction. More specifically, the PBS 78 polarizes the light to a direction (i.e., S polarization) orthogonal to the polarization direction (i.e., P polarization) of the PBS 14. The light having passed the PBS 78 is reflected by the BS 75 to be guided to the optical path of the first illuminating optical system 100*a*. As a result, the measurement light passes through the optical path of the first illuminating optical system 100*a* to be condensed at the fundus of the examinee's eye E.

The measurement light is reflected at the condensing position on the fundus (for example, the retinal surface). Fundus reflected light of the measurement light follows the optical path of the first illuminating optical system 100*a* (i.e., the optical path of the first photographing optical system 100*b*) in reverse at the time of projecting. The measurement light is reflected by the wavefront compensating device 72 in its track. The measurement light is subsequently reflected by the BS 71 and accordingly deviates from the optical path of the first illuminating optical system 100*a*. Furthermore, the measurement light is then reflected by the dichroic mirror 86 to be guided to the wavefront sensor 73 through the PBS 85, the lens 84, the planar mirror 83, and the lens 82.

The PBS 85 is a second polarizing member provided to the aberration compensating unit. The PBS 85 transmits light polarized to one direction (here, S-polarized light) out of the light with which the light source 76 has irradiated the examinee's eye E, and accordingly is used to guide the light to the wavefront sensor 73. Moreover, the PBS 85 blocks a component polarized to a direction orthogonal to the transmitted component (P-polarized light). The dichroic mirror 86 has a characteristic feature of transmitting light with substantially the same wavelength (840 nm) as the wavelength of the light from the light source 11 while reflecting light with substantially the same wavelength (780 nm) as the wavelength of the light from the light source 76 for detecting aberrations. Therefore, the wavefront sensor 73 detects the light with the S polarization component of the fundus reflected light of the measurement light. In this manner, the light reflected by the cornea and the optical device is prevented from being detected by the wavefront sensor 73.

The wavefront sensor 73 receives the fundus reflected light of the measurement light for measuring aberrations to detect the wavefront aberrations of the examinee's eye E. A device that can detect wavefront aberrations including low-order aberrations and high-order aberrations (more specifically, a Shack-Hartmann sensor, a wavefront curvature sensor that can detect changes in light intensity, and the like) may be used as the wavefront sensor 73. In the embodiment, the wavefront sensor 73 includes, for example, a microlens array including many microlenses, and a two-dimensional imaging device 73*a* (or a two-dimensional light receiving device) for receiving a light flux that has passed through the microlens array. The microlens array of the wavefront sensor 73 is placed at a position substantially conjugated with the pupil of the examinee's eye E. Moreover, an imaging surface (light receiving surface) of the two-dimensional imaging device 73*a* is placed at a position substantially conjugated with the fundus of the examinee's eye E.

A target pattern image 61 (in the embodiment, a Hartmann image) is formed by the light flux that has passed through the microlens array on the imaging surface of the two-dimensional imaging device 73*a* (the illustration is omitted). Hence, the fundus reflected light is received by the two-dimensional imaging device 73*a* through the microlens array to be imaged as a Hartmann image (dot-pattern image). In the embodiment, aberration information of the examinee's eye is acquired from the Hartmann image, and the wavefront compensating device 72 is controlled based on the aberration information. The Hartmann image will be described in detail below.

The wavefront compensating device 72 is placed in the optical path of the fundus imaging optical system 100. The wavefront compensating device 72 controls the wavefront of incident light to compensate for the wavefront aberrations of the examinee's eye E. In the embodiment, a liquid-crystal spatial optical modulator may be used as the wavefront compensating device 72. A description will be given below taking an example of a case where a reflective LCOS (Liquid Crystal On Silicon) or the like is used as the wavefront compensating device 72. In this case, the wavefront compensating device 72 is oriented in a direction where aberrations can be compensated for in a predetermined linear polarization (S polarization) such as laser light from the light source 11 (S-polarized light), fundus reflected light of the laser light (S-polarized light), and reflected light of light for detecting wavefront aberrations (S polarization component). As a result, the wavefront compensating device 72 can modulate the S polarization component of incident light. Moreover, in the embodiment, a reflective surface of the wavefront compensating device 72 is placed at a position substantially conjugated with the pupil of the examinee's eye. The wavefront compensating device 72 controls, for example, the wavefront of the reflected light from the fundus travelling to the light receiving device 56 of the fundus imaging optical system 100 to compensate for the wavefront aberrations of the examinee's eye.

In the wavefront compensating device 72 of the embodiment, the arrangement direction of liquid crystal molecules in a liquid crystal layer is substantially parallel to a polarization plane of incident reflected light. Moreover, a predetermined plane where liquid crystal molecules rotate in response to a change in voltage applied to the liquid crystal layer is placed substantially parallel to a flat plane including an incident light axis and a reflected light axis of the fundus reflected light with respect to the wavefront compensating device 72 and the normal of a mirror layer of the wavefront compensating device 72.

In the embodiment, a liquid crystal modulator, especially a reflective LCOS or the like, is used as the wavefront compensating device 72. However, the wavefront compensating device 72 is not limited to this and may be another reflective wavefront compensating device. For example, a deformable mirror being one form of MEMS (Micro Electro Mechanical Systems) may be used as the wavefront compensating device 72. Moreover, not a reflective wavefront compensating device but a transmissive wavefront compensating device may be used as the wavefront compensating device 72. The transmissive device transmits reflected light from the fundus to compensate for wavefront aberrations.

In the above description, a light source that emits illuminating light with a wavelength different from the wavelength of the light from the first light source is used as the light source for detecting aberrations. Instead of this, the first light source may also serve as the light source for detecting aberrations.

In the embodiment described above, the wavefront sensor and the wavefront compensating device are conjugated with the pupil of the examinee's eye. The wavefront sensor and the wavefront compensating device are simply required to be placed at positions substantially conjugated with a predetermined portion of the anterior segment of the examinee's eye. For example, they may be conjugated with the cornea.

Figure 3:
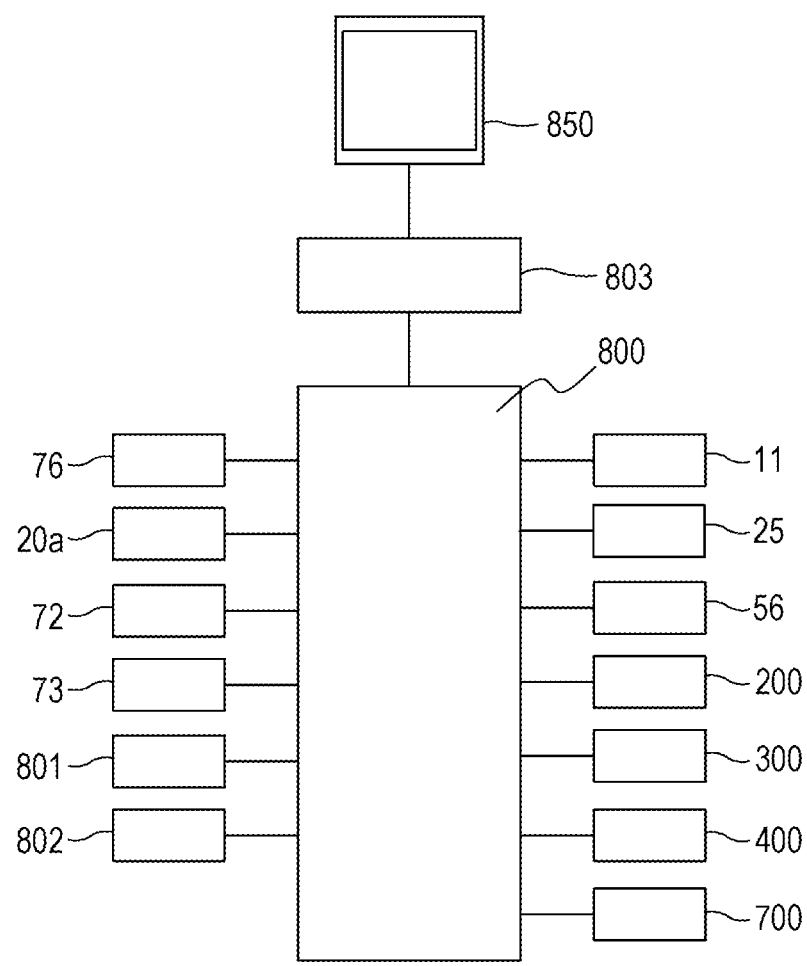
FIG. 3 is a block diagram illustrating a control system of the photographing apparatus of the embodiment.

Next, the control system of the photographing apparatus 1 in the embodiment will be described with reference to FIG. 3. The photographing apparatus 1 includes the controller 800. The controller 800 is a processor (for example, CPU) that controls the entire photographing apparatus 1. In the embodiment, the controller 800 is electrically connected to a storage unit 801, an operating unit 802, an image processor 803, and the monitor 850. Moreover, the controller 800 is electrically connected to the light source 11, the driving part 20a, the scanning unit 25, the light receiving device 56, the wavefront compensating device 72, the wavefront sensor 73, the light source 76, the second photographing unit 200, the tracking purpose unit 300, the deflecting unit 400, and the anterior segment observing unit 700.

Various control programs and fixed data are stored in the storage unit 801. Moreover, images captured by the photographing apparatus 1 and/or temporary data may be stored in the storage unit 801.

The controller 800 controls the above members such as the first photographing unit 100 based on operation signals output from the operating unit 802. The operating unit 802 is connected to an unillustrated mouse and the like as operating members operated by an examiner.

The image processor 803 forms images of the fundus of the examinee's eye having different angles of view, i.e., the first and second fundus images, on the monitor 850 based on signals received on the light receiving device 56 and the second photographing unit 200.

The monitor 850 may be a display monitor mounted on the photographing apparatus 1, or a general-purpose display monitor being a separate body from the photographing apparatus 1. Moreover, the monitor 850 may have a configuration with their combination. The monitor 850 can display the fundus images (first and second fundus images) captured by the photographing apparatus 1 in moving and still images.

The wavefront compensating device 72 is controlled by the controller 800 based on wavefront aberrations detected by the wavefront sensor 73. In the embodiment, feedback control of the wavefront compensating device 72 is executed based on a detection signal from the wavefront sensor 73. The wavefront compensating device 72 is controlled to remove the high-order aberrations of an S polarization component of reflected light of light from the light source 76, laser light emitted from the light source 11, and fundus reflected light of the laser light. In this manner, the aberrations of laser light emitted from the light source 11, and fundus reflected light of the laser light are removed. As a result, the photographing apparatus 1 acquires the first fundus image at a high resolution from which the high-order aberrations of the examinee's eye E have been removed (where the wavefront has been compensated). At this time, the low-order aberrations are corrected by the diopter correction unit 20.

A description will be given of the operation of the photographing apparatus 1 of the embodiment with the above configuration. In the photographing apparatus 1 of the embodiment, upon follow-up image capture, a baseline is registered first for the follow-up image capture. The baseline is simply required to be registered before the follow-up image capture. The baseline may be registered, for example, at a timing of acquiring a past captured image or immediately before the follow-up image capture.

In the baseline registration, the examiner selects the baseline (for example, an image as a reference for follow-up) from at least one first fundus image (first captured image) acquired in advance by the photographing apparatus 1. When the examiner selects the baseline, the controller 800 sets data indicating a photographing condition of the baseline (photographing condition data) as reference data for the follow-up image capture. One or a plurality of pieces of the reference data may be set. The reference data may be set as data attendant on the baseline.

In the follow-up image capture, for example, the examiner operates the operating unit 802 first to input, to the operating unit 802, an operation for selecting reference data to be used as a reference for the follow-up image capture from at least one or more pieces of the reference data set using the captured image as described above. The controller 800 selects reference data to be used as a reference for the follow-up image capture based on an operation signal of the operating unit 802 to reproduce the photographing condition of the reference data. As a result, the follow-up image capture becomes possible on the reproduced photographing condition of the baseline. In the embodiment, the controller 800 controls the fnidus imaging optical system 100 to reproduce the photographing condition.

The follow-up image capture here is simply required to photograph the same examinee's eye, placing a time interval from previous photographing, and is not necessarily limited to photographing for the purpose of follow-up. For example, the follow-up image capture in the embodiment includes photographing that is resumed after an intermission when an examination is performed over a long time.

In the embodiment, the controller 800 stores in advance the reference data to be used for the follow-up image capture in the storage unit 801. In other words, the controller 800 stores photographing condition data related to the image captured in advance as the reference data in the storage unit 801.

Here, the reference data contains at least one of information on a photographing position, information on the aberrations of the examinee's eye, and information on a pupil position of an anterior segment image. For example, information on a photographing position on the fundus of a captured image, and a scan range of the deflecting unit 400 of when the captured image was obtained, coordinates of the first fundus image on the second fundus image, and the baseline itself (the details are described below) may be used as the information on the photographing position. Moreover, the information on the photographing position on the fundus may contain information on a region of interest being part of the captured image. The region of interest may be a ROI described below. In this case, the controller 800 may acquire a cell image newly formed based on a signal from the light receiving device 56, the cell image including the region of interest, as the captured image obtained by the follow-up image capture (the second captured image).

Specific examples of the information on the aberrations of the examinee's eye can include a wavefront aberration amount detected by the wavefront sensor 73 at the time of acquisition of the captured image, position information of optical members (in the embodiment, mirrors and lenses) included in the diopter correction unit 20, information on the amount of aberrations corrected by the diopter correction unit 20 at the time of acquisition of the captured image, and a measurement result of drive information of the wavefront compensating device 72. The drive information may be drive condition data of the wavefront compensating device 72 at the time of acquisition of the captured image (for example, the drive amount of the wavefront compensating device 72 at the time of acquisition of the captured image), or wavefront aberration data of the examinee's eye constituting the basis of the drive condition.

The operation of the apparatus will be described below with reference to a flowchart illustrated in FIG. 4. After being turned on, the photographing apparatus 1 operates in accordance with a program for a main process stored in the storage unit 801. In the photographing apparatus 1 of the embodiment, normal image capture where the examiner sets a photographing condition freely to photograph the first fundus image, and the above-mentioned follow-up image capture where a photographing condition of past photographing is reproduced are practicable. Moreover, in the photographing apparatus 1, a captured image of the first fundus image acquired in advance is used to set the baseline.

In the embodiment, either one of the normal image capture and the follow-up image capture is performed in accordance with an instruction of the examiner. The controller 800 accepts a selection instruction from the examiner via the operating unit 802 (S1). The controller 800 determines a photographing method corresponding to the accepted instruction (S2), and performs photographing operations in accordance with the determination result (S3, S5).

<Normal Image Capture>

Figure 5:
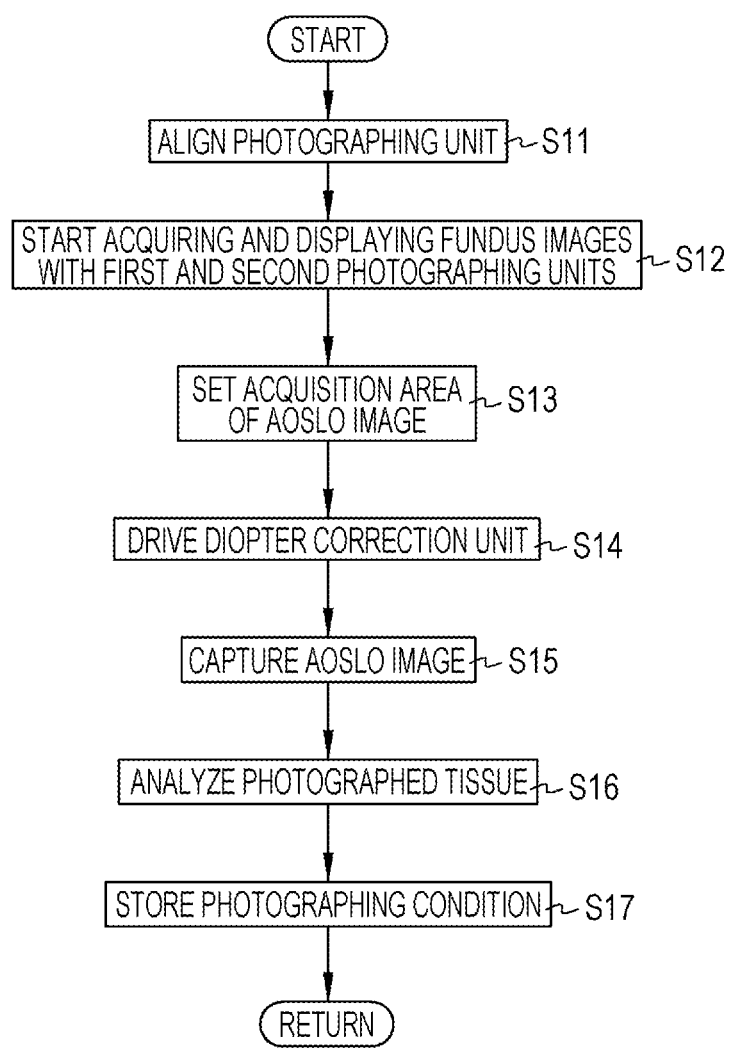
FIG. 5 is a flowchart illustrating operations of the photographing apparatus in normal image capture.

Firstly, a case where the normal image capture (S3; a photographing step, a reference data registration step) is performed will be described with reference to a flowchart of FIG. 5. Firstly, in the embodiment, the photographing unit 500 is aligned with the examinee's eye E (S11). For example, the controller 800 acquires a real-time anterior segment image using the anterior segment observing unit 700 and also displays the anterior segment image (front image) on the monitor 850. While observing the anterior segment image on the monitor 850, the examiner roughly adjusts alignment by making position adjustment of the chin support 610 manually or automatically. In this case, the examiner instructs the examinee to fixate an unillustrated fixation target.

Figure 6:
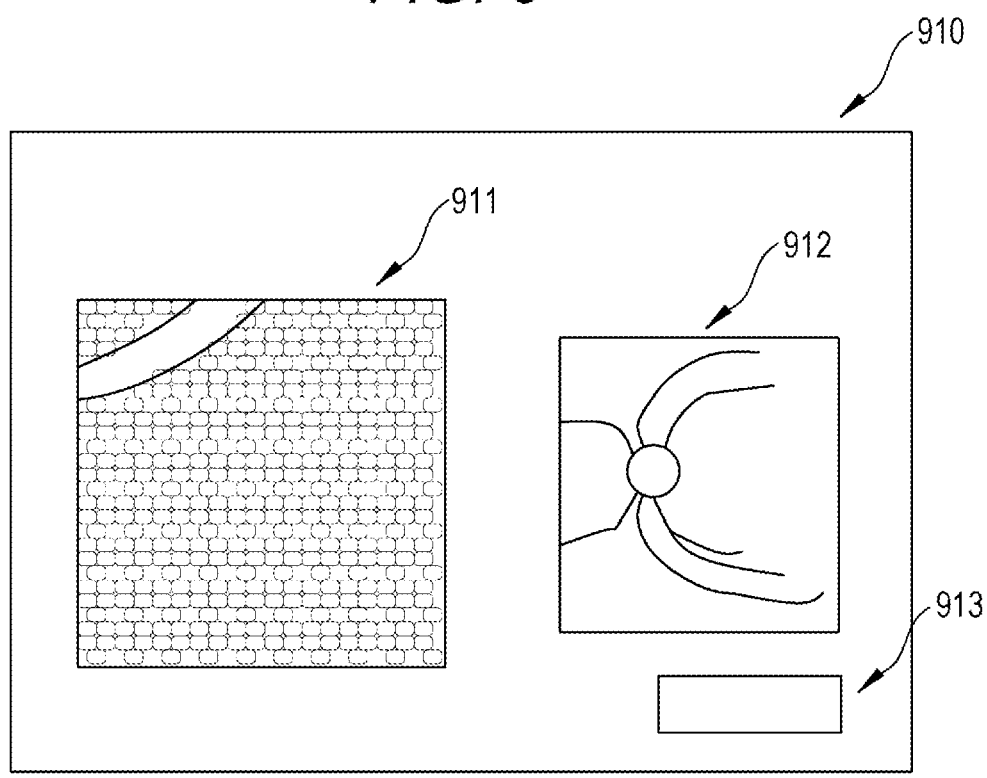
FIG. 6 is a diagram illustrating a standard screen.

In the embodiment, after the rough alignment is complete, when the examiner operates a measurement switch, the acquisition and display of fundus images with the first photographing unit 100 and the second photographing unit 200 start (S12). As a result, a live image 911 of the first fundus image and a live image 912 of the second fundus image, which are acquired in real time, are displayed on a standard screen 910 of the monitor 850 (see FIG. 6).

Next, the photographing position on the fundus of the first photographing unit 100 on the fundus of the examinee's eye E (i.e., the acquisition area of the first fundus image (AOSLO image) is set (S13). In this case, the photographing position may be set at a position selected by the examiner. For example, the examiner may select a position, where an enlarged image (i.e., the first fundus image) is acquired, in the live image 912 of the second fundus image displayed on the standard screen 910. The controller 800 determines the drive area (i.e., the scan range) of the deflecting unit 400 that corresponds to the position, selected by the examiner, on the second fundus image based on an operation signal from the operating unit 802. As a result, a rough photographing position of the first fundus image is determined.

Moreover, the controller 800 adjusts the diopters of the photographing units 100 and 200 (S14). In the embodiment, the controller 800 drives diopter correction units of the photographing units 100 and 200 (for example, the diopter correction unit 20 in the first photographing unit 100) based on information on a diopter detected by a detector in the apparatus (diopter information). For example, the spherical aberration of the examinee's eye E detected by the wavefront sensor 73 is used as the diopter information. The controller 800 may perform feedback control on the diopter correction units of the photographing units 100 and 200 based on a detection signal of the wavefront sensor 73 in such a manner that the detected value of the spherical aberration becomes a target value or falls within a target range.

In the embodiment, the target value of the corrected diopter (for example, the target value of the spherical aberration) can be adjusted manually. For example, the target value is adjusted up and down by an operation via the operating unit 802. As a result, a focus position of the fundus imaging optical system 100 is adjusted in accordance with an operation by the examiner. A focus depth of the AOSLO is generally shallow. Therefore, a difference in the focus position appears easily as a difference in tissue to be photographed and observed. In the embodiment, while checking the real-time first fundus image (AOSLO image) on the monitor 850, the examiner adjusts the focus position manually. Accordingly, the focus position can be appropriately set at the tissue of the fundus desired by the examiner.

When a photographing instruction is subsequently accepted, the controller 800 captures the first fundus image (S15; a photographing step). For example, when a photographing start button 913 is selected, photographing starts. As a result, one or more first fundus images created by the image processor 803 during a photographing period are stored as captured images in the storage unit 801. At this time, the controller 800 may capture the second captured image with the second photographing unit 200 to store the captured image of the second fundus image in the storage unit 801 associating the captured image with the first fundus image. Since the wavefront compensating device 72 is placed in the fundus imaging optical system 100, the photographing is performed in a state where the wavefront aberrations of the examinee's eye have been compensated for.

Here, the controller 800 may use the captured first fundus image to make an analysis of the tissue of the fundus of the examinee's eye (S16). At this time, the image used for the analysis may be an averaged image formed from a plurality of the first fundus images. For example, in the embodiment, an analysis of photoreceptor cells may be made. In the analysis of photoreceptor cells, the controller 800 obtains, for example, information on the density of photoreceptor cells (for example, the density of photoreceptor cells, and the area of the photoreceptor cells) and/or information on the distribution/arrangement of the photoreceptor cells (for example, the shape distribution of the photoreceptor cells, and the incidence of a hexagonal cell). The controller 800 stores the analysis result in the storage unit 801 associating the analysis result with the captured image. The controller 800 may store, in the storage unit 801, the analyzed region on the captured image set upon the analysis of the photoreceptor cells, together with the analysis result.

Moreover, in the embodiment, the controller 800 stores, in the storage unit 801, photographing condition data of the captured image together with the captured image of the first fundus image (S17; reference data registration step). Here, the controller 800 stores, in the storage unit 801, the photographing condition including the information on the photographing position and the information on the aberrations of the examinee's eye. Moreover, the controller 800 may also use the result of the analysis process (S16) as a kind of the photographing condition.

<Registration of Baseline>

Figure 4:
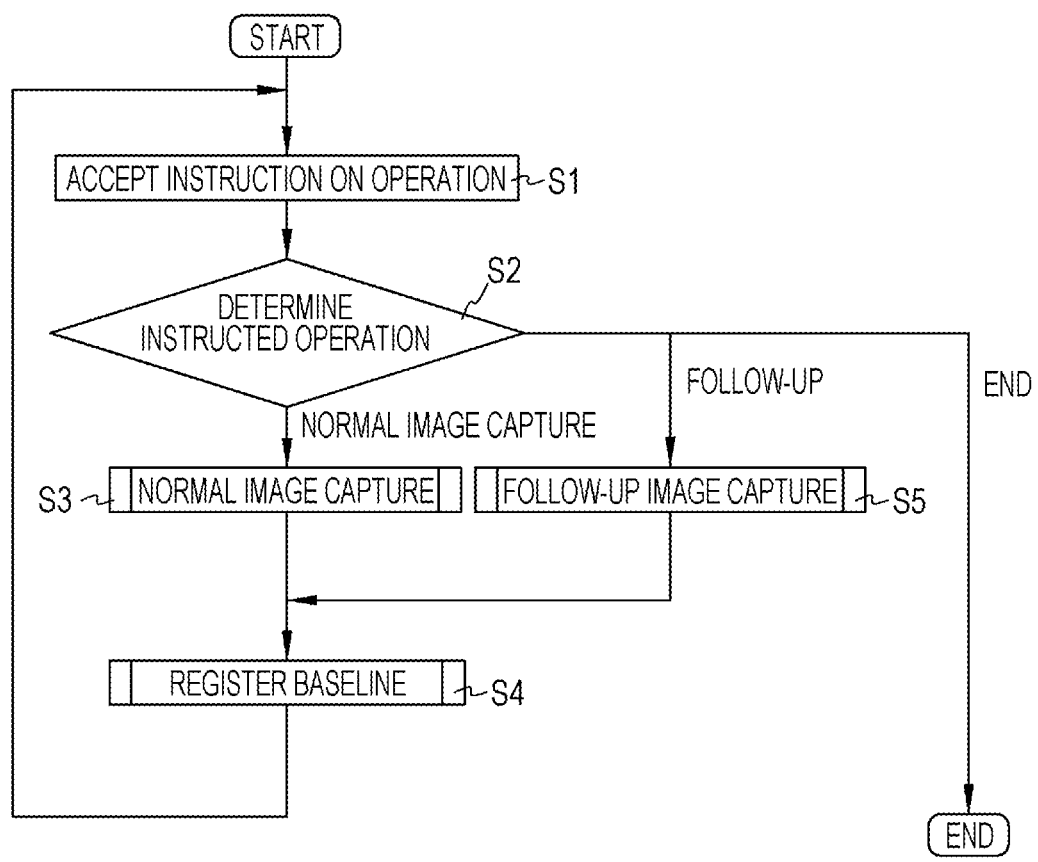
FIG. 4 is a flowchart illustrating operations of the photographing apparatus in a main process.

As illustrated in FIG. 4, in the embodiment, after the photographing of the first fundus images is complete, the controller 800 performs a process for registering the baseline (S4). The examiner selects a first fundus image to be registered as the baseline from, for example, captured image(s) of one or more first fundus images captured in advance. In this case, for example, the controller 800 may display, on the monitor 850, a selection screen 920 (see FIG. 7) for selecting the baseline.

Figure 7:
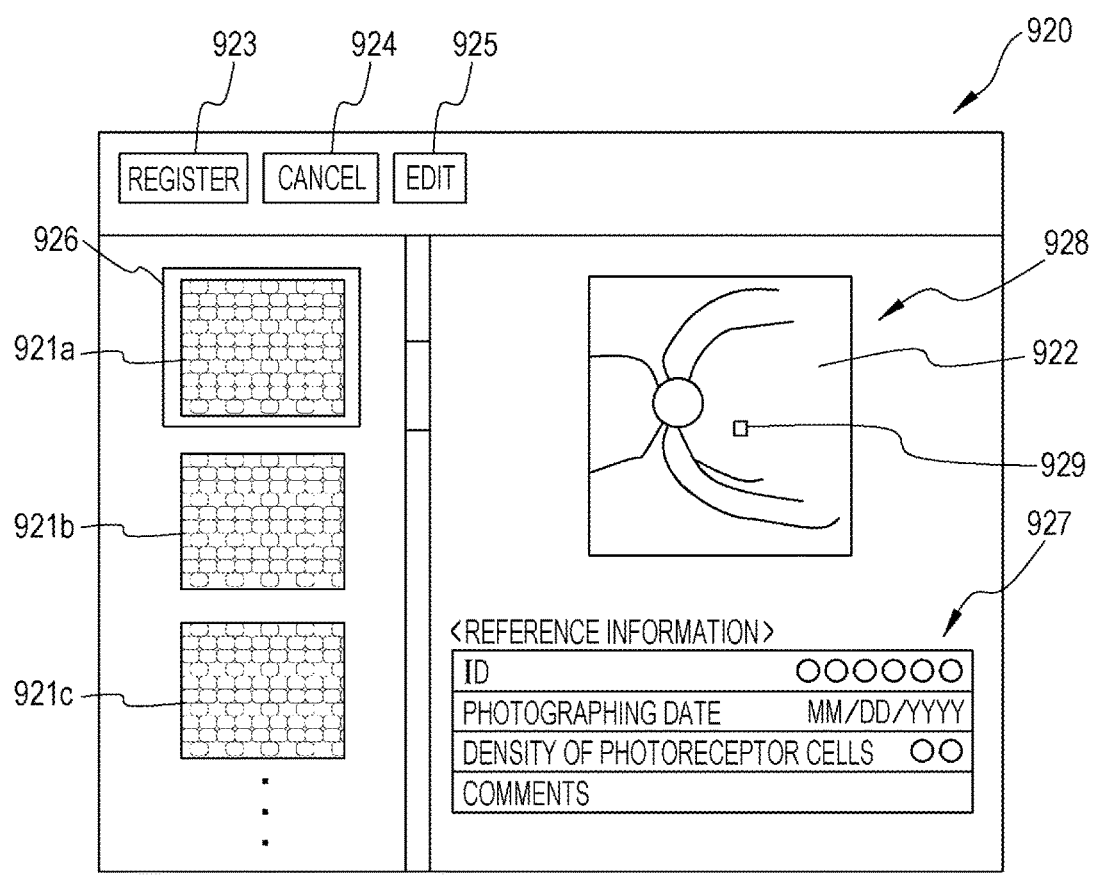
FIG. 7 is a diagram illustrating a selection screen.

As an example, as illustrated in FIG. 7, for example, first fundus images (captured images) 921 (921a, 921n, 921c, . . . ), a register button 923, a cancel button 924, and an edit button 925 are displayed on the selection screen 920. The first fundus images 921 displayed on the selection screen 920 are captured images to be candidates for the baseline. Identification information of each captured image, such as information indicating a photographing condition, photographing date, and patient, together with the first fundus image 921, is displayed on the selection screen 920. Various pieces of information may be displayed in text format, or image format. The examiner operates a pointing device and the like and selects one first fundus image 921. As a result, the selected first fundus image 921 is enclosed in a frame 926. Moreover, in the embodiment, text information 927 and image information 928, which are reference information on the selected first fundus image 921, are displayed on the selection screen 920. The reference information is information for identifying a captured image, and contains the identification information such as information indicating a photographing condition, photographing date, and patient. In FIG. 7, a patient ID, photographing date, analysis result, and comments (for example, title) are displayed as the text information 927. The examiner selects the edit button 925 to enable the edition of the text information 927. Moreover, for example, the image information (graphic) 928 indicating a photographing position on the first fundus image 921 selected by the examiner is displayed as the image information 928. In the embodiment, the photographing position of the first fundus image 921 is indicated by a mark 929 on a second fundus image 922.

The examiner selects the register button 923, and accordingly, the controller 800, in the storage unit 801, stores the first fundus image 921 enclosed in the frame 926 as the baseline. Moreover, the controller 800 stores photographing condition data of the captured image in the memory (the storage unit 801), associating the photographing condition data with the baseline. The baseline is set and managed for each patient. In other words, the baseline is stored in the storage unit 801 for each patient ID. The examiner selects the cancel button 924 and accordingly can finish the registration of the baseline.

As described above, the baseline for the follow-up image capture is registered based on the captured image. In the embodiment, as an example, upon image capturing, whether or not to set a captured image obtained in the image capturing as the baseline is selected. Not limited to this, and the photographing apparatus 1 according to the embodiment is simply required to be configured such that an image captured in advance is able to be registered as the baseline.

<Follow-Up Image Capture>

Next, detailed operations in the follow-up image capture (S5; a photographing condition reproduction step) will be described with reference to a flowchart of FIG. 8. Firstly, the photographing unit 500 is aligned with the examinee's eye E (S11). Moreover, the acquisition and display of fundus images with the first photographing unit 100 and the second photographing unit 200 start, and consequently the standard screen 910 is displayed on the monitor 850 (S12). The operations of S11 and S12 are similar to the normal image capture, and therefore their descriptions are omitted. The operations of S11 and S12 may be omitted when being complete in advance in the normal image capture or the like.

Next, in the photographing apparatus (ophthalmic apparatus) 1, the controller 800 performs an operation for setting a photographing condition used in the follow-up image capture (S23 to S25). In the embodiment, the photographing condition to be used in the follow-up image capture is set in accordance with a first fundus image to serve as the baseline. For example, the controller 800 displays a baseline selection screen 930 (see FIG. 9) on the monitor 850 to allow the examiner to select the baseline (S23). Then, the controller 800 accepts a baseline selection instruction via the operating unit 802 (S24).

Figure 9:
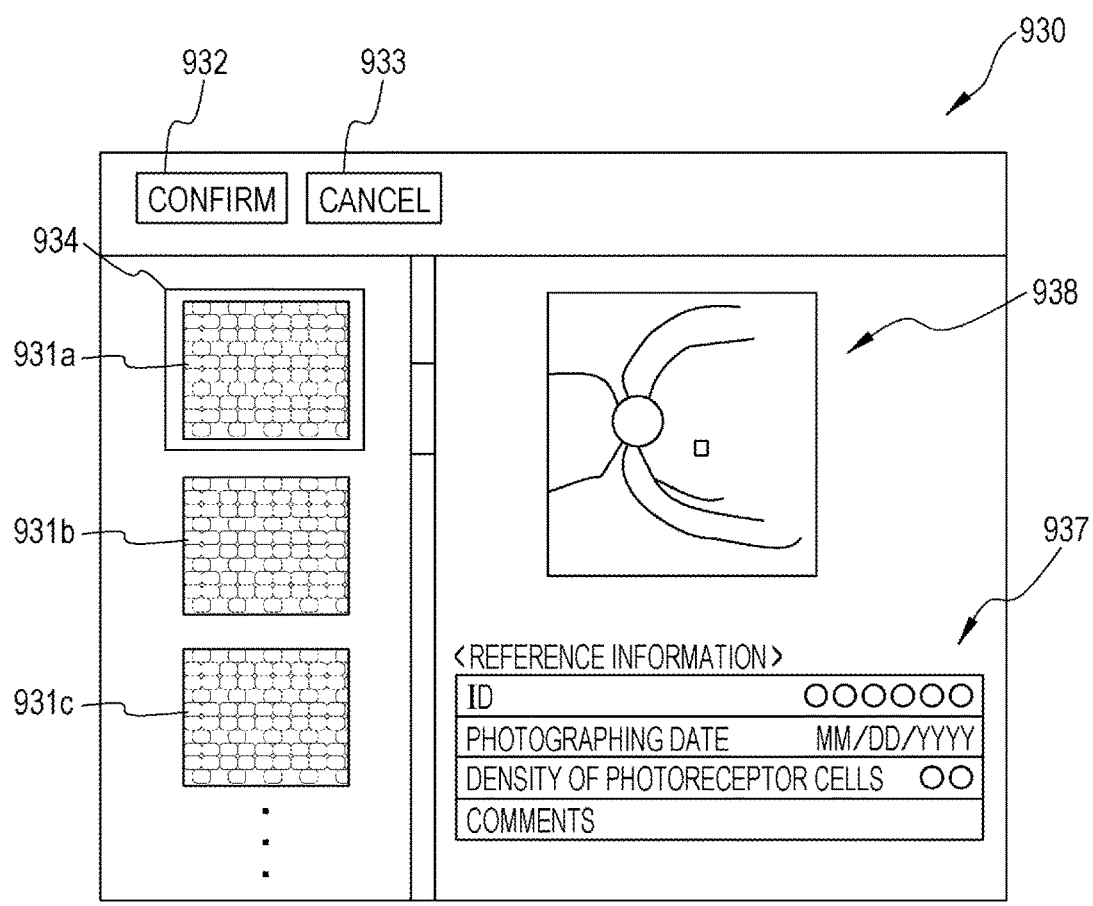
FIG. 9 is a diagram illustrating a baseline selection screen.

A group 931 of a plurality of baselines is displayed on the baseline selection screen 930 illustrated as an example in FIG. 9. In the baseline group 931, a plurality of baselines 931a, 931b, 931c, . . . is arranged to be displayed. A confirm button 932, a cancel button 933, and the like, in addition to the above baseline group 931, are displayed on the baseline selection screen 930.

The examiner selects a baseline to be used for the follow-up image capture from the baseline group 931 using the pointing device and the like. The controller 800 displays a frame 934 enclosing the selected baseline (here, the baseline 931a). Moreover, for example, identification information of each baseline, such as information indicating a photographing condition, photographing date, and a patient, is displayed as reference information 937 and 938 on the baseline selection screen 930. Hence, the examiner can grasp a photographing condition and photographing purpose of a baseline by checking the reference information 937 and 938 of each baseline. As a result, the examiner can grasp a photographing condition of each baseline based on its reference information. The contents of the reference information 937 and 938 illustrated in FIG. 9 are similar to the reference information (the text information 927 and the image information 928) illustrated on the baseline selection screen (registration screen) 920 (see FIG. 7), and therefore their descriptions are omitted. After selecting the baseline in the end, the examiner selects the confirm button 932. Accordingly, the controller 800 sets photographing condition data of the baseline enclosed in the frame 934 as reference data of the follow-up image capture (S25).

The controller 800 then controls the fundus imaging optical system 100 based on the reference data to reproduce the photographing condition upon photographing the baseline, and accordingly captures the first fundus image (S26). For example, in the embodiment, the controller 800 sets the photographing condition in the follow-up image capture so as to photograph the same tissue as the tissue of the fundus photographed in the baseline. In other words, the controller 800 controls the fundus imaging optical system 100 based on the reference data and reproduces the photographing position of the baseline.

In the embodiment, the reference data contains photographing position information for identifying the position of the tissue of the fundus photographed in the baseline, and aberration information of the examinee's eye detected upon the photographing of the baseline. For example, the controller 800 drives the aberration compensating units 20 and 72 based on the aberration information of the reference data to reproduce an aberration-corrected state in the baseline. For example, the controller 800 drives the aberration compensating units 20 and 72 in such a manner that aberrations (low-order and high-order aberration components, and the like) detected by the wavefront sensor, the amount of defocus (the amount of displacement in the optical axis direction) based on the wavefront aberrations, and the like are the same as the reference data. In this case, in terms of part of the wavefront compensating devices 20 and 72, the controller 800 may reproduce the aberration-corrected state in the baseline. For example, the controller 800 may drive the wavefront compensating device 72 to reproduce only the aberration-corrected state in the wavefront compensating device 72. Alternatively, the controller 800 may drive the diopter correction unit 20 to reproduce only the aberration-corrected state in the diopter correction unit 20. In other words, the controller 800 may control the drive of the diopter correction unit 20 so as to reproduce the aberration correction of the diopter correction unit 20 at the time of acquisition of the captured image.

Moreover, for example, the controller 800 uses scan position information (an example of position data related to a direction orthogonal to a photographing optical axis) of the reference data to reproduce the photographing position of the baseline in the direction orthogonal to the photographing optical axis (the scanning direction over the fundus). For example, when the scan position information indicates the scan range (angle) of the deflecting unit 400, the controller 800 controls the angle of each mirror of the deflecting unit 400 so as to correspond to the scan range indicated by the reference data. In other words, the controller 800 may control the scan range of the deflecting unit 400 (optical scanners) to reproduce the photographing condition on the photographing position.

The eyes always move. Hence, it is conceivable that even if the scan range of the deflecting unit 400 is set to the same range as the one upon the photographing of the baseline, the photographing position in the follow-up image capture is displaced from the photographing position of the baseline. Thus, in the embodiment, the controller 800 acquires a displacement between: the first fundus image acquired in real time by the photographing apparatus 1; and the baseline (first displacement information). The controller 800 then uses the first displacement information for capturing the first fundus image.

Figure 10:
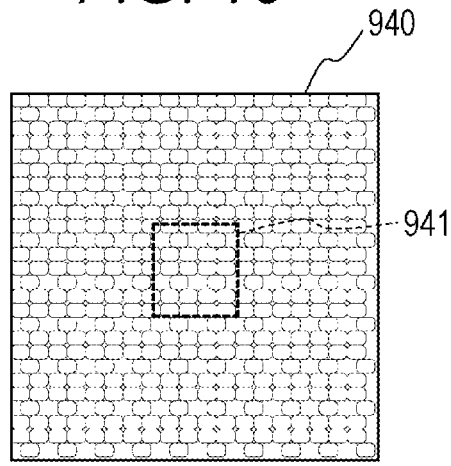
FIG. 10 is a diagram illustrating a baseline.

In the embodiment, the controller 800 sets a region used as a reference for the photographing position (hereinafter referred to as the ROI), as part of the baseline. The ROI (region of interest) of the baseline is used as a template for detecting a reference position on the fundus (i.e., the set position of the ROI in the reference image) from another first fundus image. In the embodiment, as illustrated in FIG. 10, a ROI 941 of a predetermined size is set in the center of a baseline 940. The ROI 941 may be set based on positional information on a captured image in the analyzed region used for the analysis of the photoreceptor cells. Consequently, the follow-up image capture of an image region corresponding to the analyzed region can be securely performed.

Figure 11:
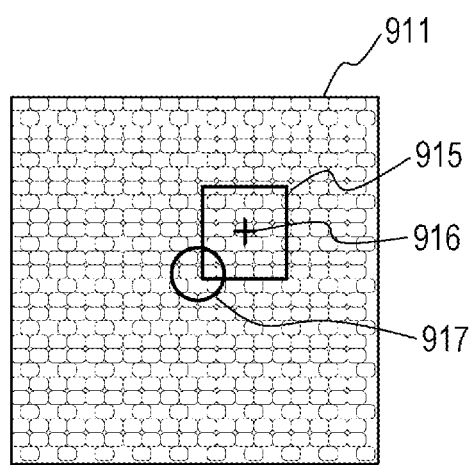
FIG. 11 is a diagram illustrating a portion where a first fundus image is displayed on the standard screen upon follow-up image capture.

When the ROI is set for the baseline, a region having a high degree of agreement with the ROI of the baseline (more specifically, a region having a high degree of agreement with a threshold value) in the live image 911 of the first fundus image displayed on the standard screen 910 is displayed enclosed in a frame 915 (see FIG. 11). Furthermore, in the embodiment, a mark 916 indicating the center of the frame 915 is displayed.

In the live image, the region enclosed in the frame 915 can be detected by various image processing methods using the ROI of the baseline and the live image (that is, the first fundus image of each frame). For example, the controller 800 may detect a region, in most agreement with the data of the image of the ROI (a position having the highest correlation), of the first fundus image, as the region enclosed in the frame 915 by moving the ROI of the baseline parallel, for one pixel at a time, with respect to the first fundus image, or rotating the ROI of the baseline by slight angles with respect to the first fundus image. The method for obtaining a correlation is not necessarily limited to this. The controller 800 may use image information on the entire reference image to obtain a correlation with another image. Moreover, various image processing methods (a method using various correlation functions, a method using the Fourier transform, or a method based on feature point matching) can be used for the detection of a correlation. A technology for detecting a displacement between images can be used for the detection of a correlation. For example, the controller 800 may determine whether or not a newly formed fundus image (first fundus image) includes the ROI (a region corresponding to the ROI (a region in the frame 915; a region of interest)). Furthermore, the controller 800 may make the determination based on a result of pattern matching between the ROI of the baseline and the newly formed fundus image.

After the setting of the ROI for the baseline, a first fundus image for a follow-up is photographed. The photographing apparatus 1 can select a mode to be automatically determined by the controller 800 (automatic photographing mode) and a mode where a photographing timing is determined by the examiner (manual photographing mode) in the photographing of the first fundus image for the follow-up. In order to do so, for example, the photographing apparatus 1 may be configured to accept a mode selection operation by the examiner via the operating unit 802 to allow the controller 800 to select a photographing mode in accordance with the operation.

<Automatic Photographing Mode>

In the automatic photographing mode of the embodiment, the controller 800 acquires an image including the ROI of the baseline, which is a live image of the newly formed first fundus image, as a captured image obtained by the follow-up image capture (the second captured image). The controller 800 may control photographing so as to place the ROI at the same position in the images between the baseline and the captured image of the follow-up. In other words, the controller 800 may control the fundus imaging optical system 100 upon the follow-up image capture so as to place the ROI at the same position in images between the baseline and the captured image for the follow-up. In this case, the ROI of the baseline does not need to perfectly coincide with the ROI of the follow-up. A displacement is acceptable to a certain degree. Moreover, in the embodiment, the controller 800 determines whether or not first fundus images sequentially formed as live images include the ROI of the baseline. The controller 800 then acquires the image based on the determination result indicating that the ROI of the baseline is included. For example, the controller 800 selects an image where the amount of displacement from the baseline satisfies an allowable range, from the sequentially formed first fundus images. The selected image is stored in the storage unit 801 to perform photographing. In this case, the controller 800 acquires, as the first displacement information, the amount of displacement between each of the first fundus images sequentially acquired by the photographing apparatus 1, and the baseline. Moreover, the controller 800 compares the amount of displacement with a threshold value. The controller 800 excludes first fundus images where the amount of displacement exceeds the threshold value from a candidate for a captured image in the follow-up image capture.

Figure 12:
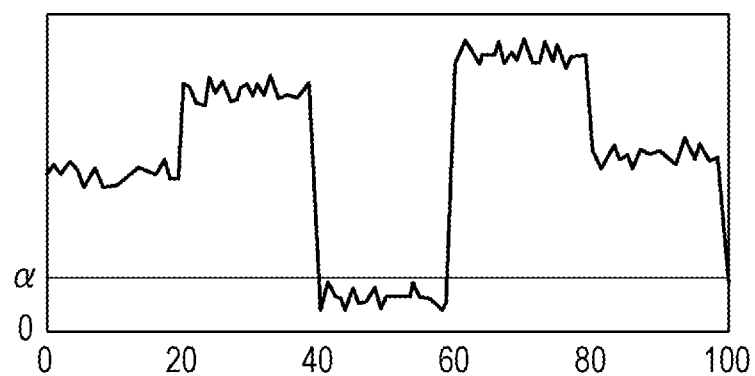
FIG. 12 is a graph illustrating the displacement of a photographing position of each frame with respect to the baseline.

FIG. 12 is a graph illustrating the amount of displacement of each first fundus image from the baseline at the time when first fundus images of 100 frames were successively acquired. In FIG. 12, the horizontal axis corresponds to the frame number indicating the photographing order. The vertical axis corresponds to the amount of displacement. In the embodiment, a threshold value α is a value smaller than a half value of the angle of view of the first fundus image (in the embodiment, 0.75 deg). As an example, in the embodiment, 0.1 deg is set as the threshold value α.

The controller 800 determines that frames having a larger amount of displacement from the baseline than the threshold value α should be excluded from the selection targets. Hence, in the example of FIG. 12, the controller 800 determines that the first fundus images other than frames 40 to 59 should be excluded from the selection targets.

Moreover, in such a scanning apparatus as illustrated by example in the photographing apparatus 1, eye movement influences the quality of an image to be acquired. In other words, as the eye movement during photographing becomes larger, the distortion of the image is increased. Hence, in the embodiment, the controller 800 uses a value indicating a relative speed between the fundus and the fundus imaging optical system at a timing when each frame was acquired (speed information) to further evaluate the first fundus image. In other words, the controller 800 compares the speed information with a threshold value. The controller 800 excludes the first fundus images whose speed information exceeds the threshold value from the candidates for the captured image in the follow-up image capture. The speed information is a value indicating a speed related to a direction orthogonal to a photographing optical axis of the fundus imaging optical system. The amount of displacement of the photographing position between adjacent frames in terms of the photographing timing is used as the speed information. The amount of displacement can be obtained as, for example, the amount of displacement between regions enclosed in the frame 915 in the frames.

Figure 13:
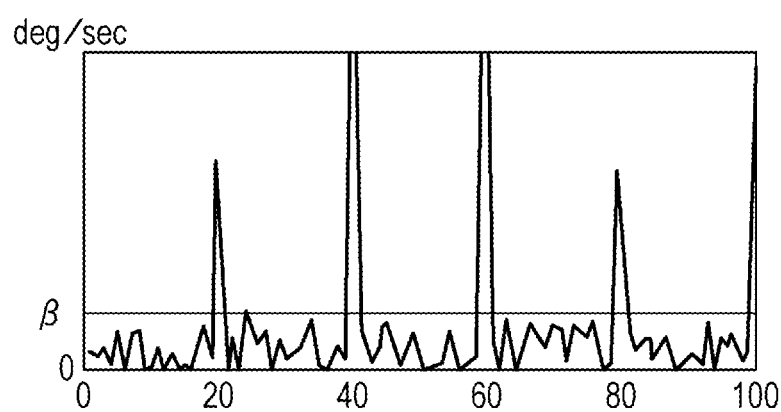
FIG. 13 is a graph illustrating a relative speed between a fundus and a fundus imaging optical system at a photographing timing of each frame.

FIG. 13 illustrates the transition of the moving speed of the fundus of the same first fundus images of 100 frames as those of FIG. 12 at their image acquisition timings. In FIG. 13, the horizontal axis corresponds to the frame number indicating the photographing order. The vertical axis corresponds to the speed. In FIG. 13, the moving speed of the n-th frame is a value obtained using the difference between the amount of displacement of the n−1-th frame and the amount of displacement of the n-th frame. In the embodiment, a threshold value β is a threshold value for excluding an image distorted due to the influence of the eye movement from the selection targets. For example, in the embodiment, β is set to exclude, from the selection targets, an image formed when a microsaccade occurs. In this case, β is preferred to be a value equal to or less than the microsaccade speed. In the embodiment, a value of 1.5 deg/sec is used as β. There are various theories on the microsaccade speed depending on documents and papers. β of the embodiment is set in such a manner that an image that is formed when the eye moves at a relatively slow speed (movement) among various theories can be excluded from the selection targets. β may be a threshold value for reducing the influence of eye movements other than the microsaccade. β may be set, for example, based on the speed of fine involuntary movement during fixation other than the microsaccade, or based on the speed of nystagmus other than the fine involuntary movement during fixation. Nystagmus other than the fine involuntary movement during fixation includes, for example, eye movements due to poor fixation and the like, and psychological eye movements that force the direction of the visual line to follow the light projected by the photographing apparatus 1 to the examinee's eye E.

The controller 800 determines that frames having a larger moving speed than the threshold value β should be excluded from the selection targets. FIG. 8 illustrates, for example, that the eye moved largely between frames 39 and 40 and between frames 59 and 60. In other words, it is conceivable that the eye moved due to microsaccades respectively between frames 39 and 40 and between frames 59 and 60. As a result, there is a high possibility of the occurrence of a large distortion due to the eye movement in frames 39 and 40 and frames 59 and 60. Hence, the controller 800 determines that theses first fundus images should be excluded from the selection targets.

Figure 8:
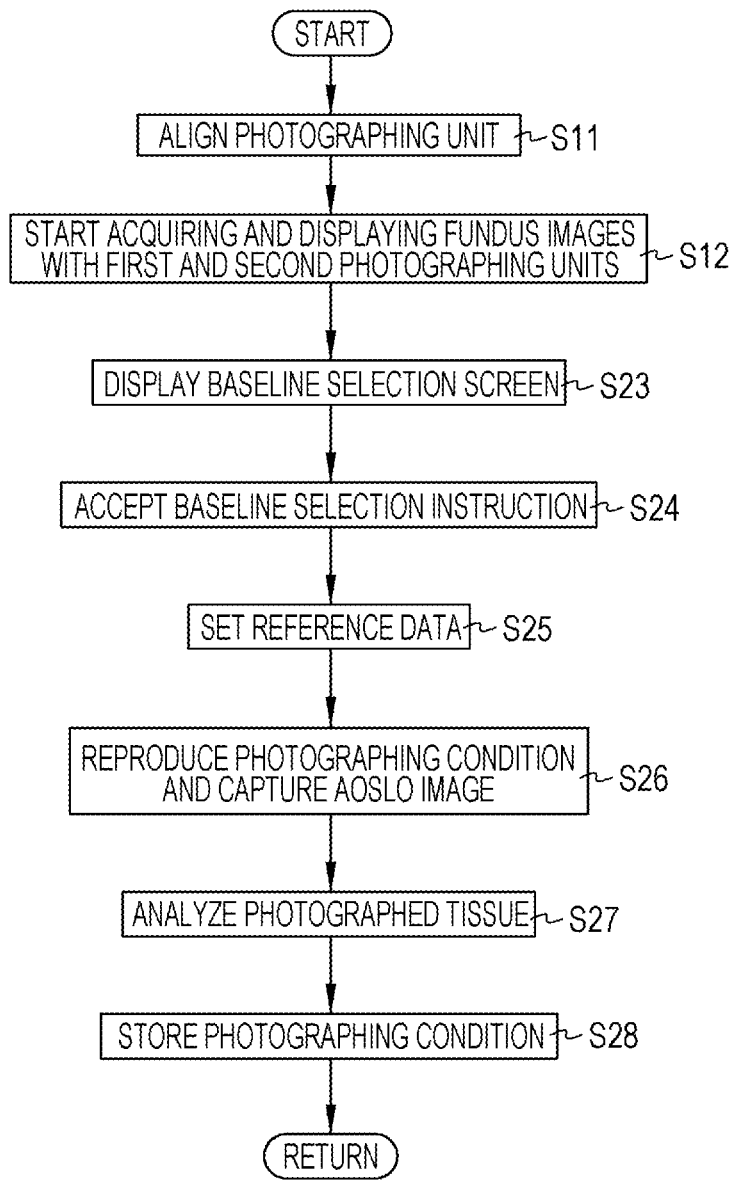
FIG. 8 is a flowchart illustrating operations of the photographing apparatus in follow-up image capture.

Therefore, in the examples of FIGS. 7 and 8, the controller 800 selects the images of frames 41 to 59 as results of the determination based on the amount of displacement between the newly acquired image and the baseline, and the determination based on the relative fundus moving speed. Moreover, the controller 800 excludes the other images from the selection targets. As a result, the controller 800 acquires first fundus images having a small amount of displacement of the photographing position from the baseline and having a small distortion, as captured images for the follow-up image capture, among the plurality of first fundus images photographed successively. In this case, the controller 800 stores, in the storage unit 801, the acquired captured images of the follow-up image capture.

In automatic photographing mode, the controller 800 may continue photographing, for example, until the examine inputs an instruction to finish photographing, or until a certain number of first fundus images is selected.

<Manual Photographing Mode>

In manual photographing mode, the tissue of the baseline is displayed in a live image. The examiner operates a photographing switch to cause the photographing apparatus 1 to photograph the first fundus image for a follow-up. In this case, the controller 800 may display, in the live image, a graphic (for example, a circle 917) indicating an allowable range of the displacement of the photographing position to allow the examiner to grasp the displacement of the live image from the baseline. In the example of FIG. 11, the center of the circle 917 is located at the central coordinates of the set position of the ROI 941 in the baseline 940 (see FIG. 10). The diameter of the circle 917 corresponds to the above-mentioned threshold value α. In the example of FIG. 11, the examiner performs a photographing operation at a timing when the mark 916 indicating the center of the frame 915 is within the circle 917. The controller 800 stores one or more first fundus images acquired at timings of inputting the photographing operation or later, as the first fundus images for the follow-up, in the storage unit 801. In this manner, manual photographing is performed. Also in manual photographing, the controller 800 may make an exclusion determination based on the above-mentioned speed information.

After the follow-up image capture is complete, the controller 800 performs a process of analyzing the photographed tissue (S27). Moreover, the controller 800 may store the photographing condition for the follow-up image capture in the storage unit 801 (S28).

As described above, in the embodiment, the photographing condition on the position of the tissue of the fundus included in the baseline photographed in advance is reproduced in the follow-up image capture. Hence, in the follow-up image capture, it becomes easy to photograph the same tissue of the fundus as the baseline. Therefore, even with an apparatus where an image to be photographed changes largely depending on the eye movement, burdens on the examiner and the examinee in the follow-up image capture are reduced.

<Comparison Display Between Baseline and Follow-Up Captured Image>

Figure 14:
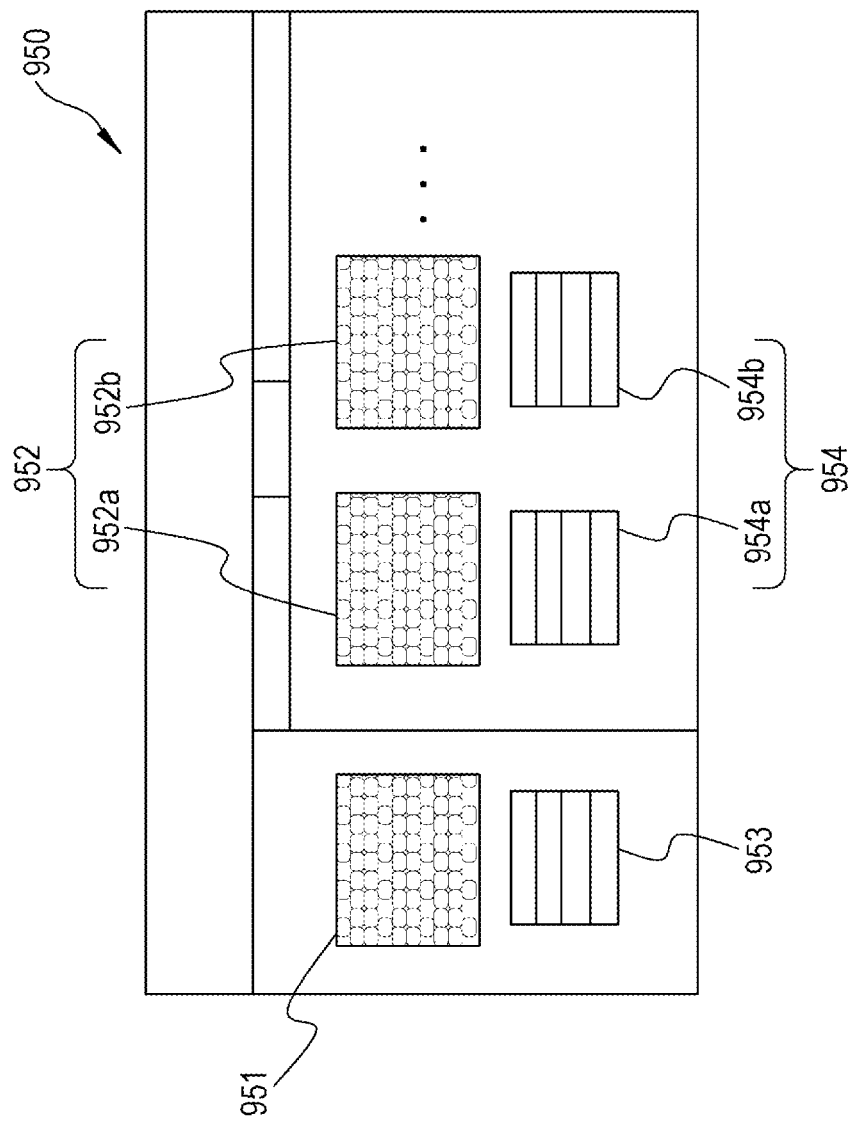
FIG. 14 is a diagram illustrating a comparison screen.

Moreover, after photographing the follow-up images, a comparison screen (see FIG. 14) between the baseline and the captured images photographed by the follow-up image capture may be displayed. A baseline 951, and captured images 952 (952a, 952b, . . . ) for the follow-up are arranged for display on a comparison screen 950 illustrated in FIG. 14. Various pieces of information 953 and 954 (954a, 954b, . . . ) such as photographing condition, analysis result, photographing date, and comments, of the baseline 951 and each of the captured images 952 for the follow-up may be arranged for display on the comparison screen 950. Moreover, comparison results such as the analysis results of the baseline and the captured images for the follow-up, and the like may be displayed on the comparison screen 950.

After the follow-up image capture is complete, the examiner and/or the controller 800 can newly register the captured image for the follow-up as the baseline (see S4 in FIG. 4). The newly registered baseline is used for the next follow-up image capture to facilitate the capture of an image with a relatively high confidence level (that is, with a small displacement of the photographing position) in the above follow-up image capture even if the condition of the tissue of the fundus is changed due to a disease, the treatment of the disease, and the like.

Up to this point the description has been given based on the embodiment. However, the technology of the present disclosure is not limited to the above embodiment, and can be modified in various manners.

For example, fixation position information may be used as the photographing position information. For example, in a case of including a configuration where a position to light a fixation light is switched between a plurality of positions, information indicating the position of a fixation light lit upon the photographing of the baseline can be used as the fixation position information. In this case, the controller 800 can reproduce the fixation position of the baseline based on the fixation position information upon the follow-up image capture.

Moreover, for example, in the above embodiment, the diopter correction unit 20 is illustrated by example as a diopter correction optical system that corrects low-order aberrations equal to or lower than two order. However, the diopter correction optical system is not limited to this. The diopter correction optical system may be configured to, for example, correct at least one of a defocus component and an astigmatic component among the wavefront aberrations. For example, an astigmatism correction optical system for correcting the astigmatic component may be provided as the diopter correction optical system. Various configurations are conceivable as the astigmatism correction optical system. The astigmatism correction optical system may include, for example, a cross cylinder lens. In this case, the astigmatism correction optical system may include a pair of cylinder lenses having an equal cylindrical power, placed in opposite orientations on the optical axis. The astigmatism correction optical system may further include a mechanism that rotates the cylinder lenses independently. The controller 800 stores, in the storage unit 801, the corrected state in the astigmatism correction optical system upon photographing the baseline. Furthermore, the controller 800 may control the drive of the astigmatism correction optical system so as to reproduce the stored corrected state upon the follow-up image capture.

Moreover, in the above embodiment, the description is given of the case where the photographing position of the baseline in the scanning direction is reproduced in the follow-up image capture as a result of image processing on a fundus image acquired by the photographing apparatus 1. However, the method for reproducing the photographing position of the baseline in the scanning direction is not necessarily limited to this. For example, the photographing position of the baseline in the scanning direction may be reproduced by physical tracking. For example, the tracking purpose unit 300 can be used for tracking. The tracking purpose unit 300 may track using the second fundus image with a wide view angle photographed by the second photographing unit 200. In the tracking here, the deflecting unit 400 is driven in such a manner that even if the examinee's eye E moves involuntarily, the movement is compensated for. See, for example, JP-A-2011-115301 for the detailed configuration of the tracking purpose unit 300 and the operation of the entire apparatus in this case. The controller 800 may be configured not to acquire the first fundus image at a timing when the deflecting unit 400 is driven by tracking. Moreover, the controller 800 may be configured in such a manner that when a first fundus image is acquired also at the timing, the image is excluded from the selection targets.

Moreover, photographing may be performed a plurality of times on the same photographing position with different amounts of defocus in the follow-up image capture. In this case, after photographing with a first amount of defocus, photographing is performed on the same photographing position with a second amount of defocus different from the first amount of defocus. In this case, for example, photographing may be performed using a plurality of pieces of reference data (for example, reference data of a plurality of captured images with different defocuses from each other and the same photographing position. Alternatively, photographing may be performed using reference data of one captured image, the reference data containing information on two or more amounts of defocus. The controller 800 may automatically continue photographing with the first amount of defocus and photographing with the second amount of defocus. Alternatively, the examiner may perform photographing manually each time. Moreover, the controller 800 and/or the examiner may perform photographing after reproducing the amount of defocus based on the wavefront aberration information and then performing wavefront compensation control based on information on a high-order aberration component from the wavefront sensor.

Moreover, the controller 800 of the photographing apparatus 1 acquires, as the reference data, for example, photographing condition data containing a measurement result of drive information for reproducing the driven state of the wavefront compensating device of when a captured image to be a baseline was acquired, and stores the photographing condition data in the storage unit 801. After that, the controller 800 may drive the wavefront compensating device 72 (for example, change the shape of a wavefront compensation region of the wavefront compensating device 72) in the follow-up image capture to reproduce a photographing condition (that is, the driven state of the wavefront compensating device) on the measurement result of the drive information. In this case, the wavefront compensating device 72 is susceptible to a quick change to a driven state that excellently corrects the aberrations of the examinee's eye. Hence, excellent follow-up image capture can be achieved.

In the above embodiment, if the first fundus image is registered as the baseline, the examiner visually checks captured images (first fundus images) and selects an excellent image from the captured images of the first fundus images. However, the image registered as the baseline is not necessarily selected based on an instruction of the examiner. For example, the controller 800 can also obtain qualities of a plurality of captured images obtained as a result of photographing to automatically set an excellent quality image as the baseline. For example, in a proposed method, when photoreceptor cell images are obtained as the first fundus images, a plurality of captured images obtained as a result of photographing is frequency-transformed (for example, Fourier-transformed) to obtain a luminance histogram of the frequency images. The histogram is used to evaluate the quality of the image of the photoreceptor cells. Here, the evaluation result of the quality of the captured image is described as information used by the controller 800 to automatically register the baseline. However, the handling of the evaluation result is not necessarily limited to this. For example, as in the above embodiment, the controller 800 may display, on the monitor 850, the evaluation result of the quality of each captured image as one piece of reference information for the time when the examiner registers the baseline manually.

Moreover, the captured images obtained by the follow-up image capture in the above embodiment may be used to evaluate (more specifically, converted into numbers) the reproducibility of the density of photoreceptor cells for each examinee's eye. The reproducibility here is described. The controller 800 (the photographing apparatus 1), for example, performs photographing a plurality of times on the same examinee for a short period of time (for example, one day) to acquire a captured image photographed at each timing during that period. The controller 800 calculates the quality of each captured image. Moreover, the controller 800 selects the baseline from the captured images. At this point in time, an image having the highest quality is selected as the baseline. Moreover, the controller 800 sets a threshold value for comparing image qualities based on the image quality of the baseline. Next, the controller 800 selects captured images having a higher quality than the threshold value from the captured images other than the baseline. The controller 800 then derives the distribution of the density of photoreceptor cells of each selected captured image and the baseline. The value of the distribution can be used as a value indicating reproducibility. For example, the density of photoreceptor cells of a captured image photographed in the follow-up image capture performed for a follow-up may be included in the range of the distribution of the density of photoreceptor cells of the baseline. This may serve as a guideline to allow the examiner to consider that, for example, there is no significant change in the density of photoreceptor cells and the change falls within a margin of error. On the other hand, the density of photoreceptor cells obtained in the follow-up image capture may be beyond the range of the distribution of the density of photoreceptor cells of the baseline. This serves as a guideline to allow the examiner to consider that there is a significant change in the density of photoreceptor cells.

Moreover, in the above embodiment, the case of making an analysis of photoreceptor cells is described. Instead of this, an analysis of tissue other than the photoreceptor cells (for example, a blood vessel) may be made.

In the above embodiment, the wavefront sensor 73 is provided to the optical system of the photographing apparatus 1 as a wavefront measuring device that measures the wavefront aberrations of the examinee's eye E. However, the photographing apparatus 1 does not necessarily include the wavefront sensor 73. The photographing apparatus 1 is simply required to include a wavefront measuring device that measures the wavefront aberrations of the examinee's eye based on reflected light from the fundus. For example, a device that measures wavefront aberrations using the Phase Diversity technique is conceivable as the wavefront measuring device. In the Phase Diversity technique, an image obtained by giving measurement light having known wavefront aberrations called Phase Diversity on purpose to a target optical system (here, the examinee's eye) is used for image processing. Consequently, the wavefront aberrations of the target optical system are estimated. The measurement light with Phase Diversity can be generated by, for example, controlling the wavefront compensating device 72 in a predetermined state. Naturally, the measurement light having Phase Diversity may be generated by another method.

In the above description, a confocal optical system (SLO optical system) is used as the fundus imaging optical system 100. In the confocal optical system, a light flux reflected from the fundus of the examinee's eye is received via a confocal opening placed at a position substantially conjugated with the fundus of the examinee's eye. Accordingly, a confocal front image of the fundus of the examinee's eye is photographed (see, for example, JP-T-2001-507258).

However, the fundus imaging optical system 100 is not limited to the confocal optical system. The fundus imaging optical system 100 may be, for example, a fundus camera optical system. The fundus camera optical system receives a light flux reflected from the fundus of the examinee's eye with a two-dimensional imaging device to photograph a front image of the fundus of the examinee's eye E. Alternatively, the fundus imaging optical system 100 may be an optical coherence tomography optical system (OCT optical system). The optical coherence tomography optical system receives interference light between the light flux reflected from the fundus of the examinee's eye and reference light to photograph a tomographic image of the examinee's eye E.

The embodiment also relates to a fundus photographing apparatus with wavefront compensation that photographs a fundus image of an examinee's eye in a state where the wavefront aberrations of the examinee's eye have been corrected, and a method for photographing the fundus image.

In manual photographing mode, when the tissue of the baseline is displayed in a live image, the examiner may operate the photographing switch to cause the photographing apparatus 1 to photograph the first fundus image for a follow-up.

β in the embodiment may be set in such a manner that even at a relatively slow movement among various theories, an image formed upon the movement can be excluded from the selection targets.

Various pieces of information 953 and 954 (954a, 954b . . . ) such as photographing condition, analysis result, photographing date, and comments of the baseline 951 and each captured image 952 for the follow-up may be arranged for display on the comparison screen 950.

The Phase Diversity technique can also be said for carrying out image processing using an image obtained by giving measurement light with known wavefront aberrations called Phase Diversity on purpose to a target optical system (here, the examinee's eye) to estimate the wavefront aberrations of the target optical system.

The embodiment may be the following first to tenth fundus photographing apparatus with wavefront compensation, and a method for photographing the first fundus photographing apparatus with wavefront compensation.

The first fundus photographing apparatus with wavefront compensation includes: a fundus imaging optical system for receiving a reflected light from the fundus of an examinee's eye with a light receiving device to acquire a cell image of the fundus; a wavefront compensating device placed in an optical path of the fundus imaging optical system, for controlling the wavefront of incident light to compensate for the wavefront aberrations of the examinee's eye; and a controller for executing a photographing step of acquiring a first captured image being a captured image of the cell image based on a signal from the light receiving device in a state where the wavefront aberrations have been compensated for, a reference data registration step of acquiring photographing condition data on the first captured image as reference data for follow-up image capture, and storing the photographing condition data in a storage unit, and a photographing condition reproduction step of selecting reference data for the follow-up image capture from one or more pieces of the reference data stored in advance in the storage unit in the reference data registration step based on an operation input from an examiner, and reproducing a photographing condition in accordance with the selected reference data to newly acquire the cell image.

The second fundus photographing apparatus with wavefront compensation is the first fundus photographing apparatus with wavefront compensation. The controller, in the reference data registration step, includes a measurement result of drive information for reproducing a driven state of the wavefront compensating device of when the first captured image was acquired, in the photographing condition data acquired and stored as the reference data, and in the photographing condition reproduction step, reproduces a photographing condition related to the measurement result.

The third fundus photographing apparatus with wavefront compensation is the second fundus photographing apparatus with wavefront compensation. The controller, in the photographing condition reproduction step, changes the shape of a wavefront compensation region in the wavefront compensating device to reproduce the measurement result.

The fourth fundus photographing apparatus with wavefront compensation is the first fundus photographing apparatus with wavefront compensation, and further includes a correction optical system, provided separately from the wavefront compensating device, for correcting at least one of a defocus component and an astigmatic component among the wavefront aberrations. The controller controls the wavefront compensating device and the correction optical system based on the wavefront aberrations of the examinee's eye measured by a wavefront measuring device to correct the wavefront aberrations of the examinee's eye, and includes information on the amount of aberration correction by the correction optical system of when the first captured image was acquired in the photographing condition data acquired and stored as the reference data in the reference data registration step, and controls the drive of the correction optical system in the photographing condition reproduction step so as to reproduce the aberration correction of the correction optical system of when the first captured image was acquired.

The fifth fundus photographing apparatus with wavefront compensation is the first fundus photographing apparatus with wavefront compensation. The controller, in the reference data registration step, includes information on a photographing position on the fundus in the first captured image in the photographing condition data acquired and stored as the reference data, and in the photographing condition reproduction step, controls the fundus imaging optical system based on the information on the photographing position to reproduce the photographing condition related to the photographing position.

The sixth fundus photographing apparatus with wavefront compensation is the fifth fundus photographing apparatus with wavefront compensation. The fundus imaging optical system has an optical scanner for scanning the fundus with light to obtain the reflected light. The controller, in the photographing condition reproduction step, controls a scan range of the optical scanner to reproduce the photographing condition related to the photographing position.

The seventh fundus photographing apparatus with wavefront compensation is the fifth fundus photographing apparatus with wavefront compensation. The information on the photographing position on the fundus contains information on a region of interest being part of the first captured image. The controller, in the photographing condition reproduction step, acquires a cell image newly formed based on a signal from the light receiving device, the cell image including the region of interest, as a second captured image by the follow-up image capture.

The eighth fundus photographing apparatus with wavefront compensation is the seventh fundus photographing apparatus with wavefront compensation. The controller, in the photographing condition reproduction step, controls the fundus imaging optical system so as to place the region of interest at the same position of images between the first and second captured images to acquire the second captured image.

The ninth fundus photographing apparatus with wavefront compensation is the seventh fundus photographing apparatus with wavefront compensation. The controller, in the photographing condition reproduction step, determines whether or not the region of interest is included in the newly formed fundus image.

The tenth fundus photographing apparatus with wavefront compensation is the ninth fundus photographing apparatus with wavefront compensation. The controller makes the determination in the photographing condition reproduction step based on a result of pattern matching between the region of interest of the first captured image and the newly formed fundus image.

The photographing method of the first fundus photographing apparatus with wavefront compensation includes: a reference data registration step of acquiring photographing condition data on a cell image of a fundus acquired as a captured image with the fundus photographing apparatus with wavefront compensation, as reference data for follow-up image capture on the cell image; and a photographing condition reproduction step of selecting reference data for the follow-up image capture from one or more pieces of the reference data stored in advance in the storage unit based on an operation input from the examiner, and reproducing a photographing condition in accordance with the selected reference data to newly acquire the cell image.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A fundus photographing apparatus with wavefront compensation, comprising:
   a fundus imaging optical system that receives a reflected light from fundus of an examinee's eye with a light receiving device to acquire a cell image of the fundus;
   a wavefront compensating device placed in an optical path of the fundus imaging optical system to compensate for wavefront aberrations of the examinee's eye by controlling a wavefront of the reflected light;
   a controller that executes
      a photographing step that acquires a first captured image being a captured image of the cell image based on a signal from the light receiving device in a state where the wavefront aberrations are compensated for,
      a reference data registration step that acquires photographing condition data on the first captured image as reference data for follow-up image capture and storing the photographing condition data in a storage unit, and
      a photographing condition reproduction step that selects, based on an operation input from an examiner, reference data for the follow-up image capture from one or more pieces of the reference data stored in advance in the storage unit in the reference data registration step, and reproducing a photographing condition in accordance with the selected reference data to newly acquire the cell image;
   a correction optical system provided separately from the wavefront compensating device to correct at least one of a defocus component and an astigmatic component among the wavefront aberrations; and
   a wavefront measuring device that measures the wavefront aberrations of the examinee's eye, wherein
   the controller controls the wavefront compensating device and the correction optical system based on the wavefront aberrations of the examinee's eye measured by the wavefront measuring device to correct the wavefront aberrations of the examinee's eye,
   in the reference data registration step, the controller includes information on the amount of aberration correction by the correction optical system of when the first captured image was acquired, in the photographing condition data acquired and stored as the reference data, and
   in the photographing condition reproduction step, the controller controls the drive of the correction optical system so as to reproduce the aberration correction of the correction optical system of when the first captured image was acquired.

2. The fundus photographing apparatus with wavefront compensation according to claim 1, wherein
   in the reference data registration step, the controller includes a measurement result of drive information for reproducing a driven state of the wavefront compensating device at a time of acquisition of the first captured image, in the photographing condition data acquired and stored as the reference data, and
   in the photographing condition reproduction step, the controller reproduces the driven state of the wavefront compensating device.

3. The fundus photographing apparatus with wavefront compensation according to claim 2, wherein the controller, in the photographing condition reproduction step, changes the shape of a wavefront compensation region in the wavefront compensating device to reproduce the driven state of the wavefront compensating device.

4. The fundus photographing apparatus with wavefront compensation according to claim 1, wherein
   in the reference data registration step, the controller includes information on a photographing position on the fundus in the first captured image, in the photographing condition data acquired and stored as the reference data, and
   in the photographing condition reproduction step, the controller controls the fundus imaging optical system based on the information on the photographing condition to reproduce the photographing condition related to the photographing position.

5. The fundus photographing apparatus with wavefront compensation according to claim 4, wherein
   the fundus imaging optical system includes an optical scanner for scanning the fundus with light to obtain the reflected light, and
   the controller controls a scan range of the optical scanner in the photographing condition reproduction step to reproduce the photographing condition related to the photographing position.

6. The fundus photographing apparatus with wavefront compensation according to claim 4, wherein
   the information on the photographing position on the fundus includes information on a region of interest being part of the first captured image, and
   in the photographing condition reproduction step, the controller acquires a cell image newly formed based on a signal from the light receiving device, the cell image including the region of interest, as a second captured image by the follow-up image capture.

7. The fundus photographing apparatus with wavefront compensation according to claim 6, wherein
   upon acquiring the second captured image in the photographing condition reproduction step, the controller controls the fundus imaging optical system so as to place the region of interest at the same position of images between the first and second captured images.

8. The fundus photographing apparatus with wavefront compensation according to claim 6, wherein
   in the photographing condition reproduction step, the controller determines whether or not the region of interest is included in the newly formed fundus image.

9. The fundus photographing apparatus with wavefront compensation according to claim 8, wherein
   the controller makes the determination in the photographing condition reproduction step based on a result of pattern matching between the region of interest of the first captured image and the newly formed fundus image.

* * * * *